US007820840B2

(12) United States Patent
Linic et al.

(10) Patent No.: US 7,820,840 B2
(45) Date of Patent: Oct. 26, 2010

(54) EPOXIDATION CATALYST AND PROCESS

(75) Inventors: Suljo Linic, Ann Arbor, MI (US); Phillip Christopher, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/498,942

(22) Filed: Jul. 7, 2009

(65) Prior Publication Data

US 2010/0010243 A1 Jan. 14, 2010

Related U.S. Application Data

(60) Provisional application No. 61/079,368, filed on Jul. 9, 2008.

(51) Int. Cl.
*C07D 301/10* (2006.01)
(52) U.S. Cl. ......................... 549/534; 502/347
(58) Field of Classification Search ............... 502/347; 549/534
See application file for complete search history.

(56) References Cited

U.S. PATENT DOCUMENTS

| 2,279,469 | A | 4/1942 | Law et al. |
|---|---|---|---|
| 2,279,470 | A | 4/1942 | Law et al. |
| 5,008,413 | A | 4/1991 | Liu |
| 5,374,748 | A | 12/1994 | Rizkalla |
| 5,387,751 | A | 2/1995 | Hayden et al. |
| 5,663,385 | A | 9/1997 | Kemp |
| 5,780,657 | A | 7/1998 | Cooker et al. |
| 5,905,053 | A | 5/1999 | Rizkalla et al. |
| 5,965,480 | A | 10/1999 | Cooker et al. |
| 6,750,173 | B2 | 6/2004 | Rizkalla et al. |
| 2004/0224841 | A1 | 11/2004 | Matusz et al. |
| 2005/0056118 | A1 | 3/2005 | Xia et al. |

FOREIGN PATENT DOCUMENTS

| JP | 54-115306 | 9/1979 |
|---|---|---|
| JP | 2002-510306 | 4/2002 |

OTHER PUBLICATIONS

Williams et al., J. Am. Chem. Soc., 2004, 126, 8509-8514.*
Campbell, "The selective epoxidation of ethylene catalyzed by Ag(111): a comparison with Ag(110)," *J. Catal.*, 94:436-444 (1985).
Kokalj et al., "Adsorption of ethylene on stepped Ag(n10) surfaces," Conference presentation at the 22nd European Conference on Surface Science (Sep. 8, 2003).
Sajkowski et al., "Structure sensitivity of the catalytic oxidation of ethene by silver," *Catal. Rev. Sci. Eng.*, 29:325-60 (1987).
Sun et al., "Large-scale synthesis of uniform silver nanowires through a soft, self-seeding, polyol process," *Adv. Mater.*, 14:833-7 (2002).
Sun et al., "Shape-controlled synthesis of gold and silver nanoparticles," *Science*, 298:2176-9 (2002).
Xu, et al., "Shape-Dependent Catalytic Activity of Silver Nanoparticles for the Oxidation of Styrene," *Chemistry—An Asian Journal*, 1:888-93 (2006).
International Search Report for International Application No. PCT/US2009/049816, dated Mar. 8, 2010.
Written Opinion of the International Searching Authority, International Application No. PCT/US2009/049816, dated Mar. 8, 2010.

* cited by examiner

*Primary Examiner*—Janet L Andres
*Assistant Examiner*—David E Gallis
(74) *Attorney, Agent, or Firm*—Marshall, Gerstein & Borun LLP (57) ABSTRACT

Disclosed herein is a catalytic method of converting alkenes to epoxides. This method generally includes reacting alkenes with oxygen in the presence of a specific silver catalyst under conditions suitable to produce a yield of the epoxides. The specific silver catalyst is a silver nanocrystal having a plurality of surface planes, a substantial portion of which is defined by Miller indices of (100). The reaction is performed by charging a suitable reactor with this silver catalyst and then feeding the reactants to the reactor under conditions to carry out the reaction. The reaction may be performed in batch, or as a continuous process that employs a recycle of any unreacted alkenes. The specific silver catalyst has unexpectedly high selectivity for epoxide products. Consequently, this general method (and its various embodiments) will result in extraordinarily high epoxide yields heretofore unattainable.

40 Claims, 4 Drawing Sheets

EPOXIDATION CATALYST AND PROCESS

CROSS-REFERENCE TO RELATED APPLICATION

This application claims the benefit of U.S. provisional patent application Ser. No. 61/079,368 filed Jul. 9, 2008, the disclosure of which is incorporated herein by reference.

STATEMENT OF GOVERNMENTAL INTEREST

This invention was made with government support under grants from the U.S. Department of Energy (FG-02-05ER15686), and the National Science Foundation (CTS 0543067). The government has certain rights in the invention.

BACKGROUND OF THE INVENTION

1. Field of the Disclosure

The disclosure generally relates to methods and catalysts for the epoxidation of alkenes and, more specifically, to Ag(100) catalysts for the epoxidation of ethylene.

2. Brief Description of Related Technology

The domestic production of ethylene oxide, by the direct epoxidation of ethylene over silver (Ag) catalysts, yields about 10 billion pounds of ethylene oxide per year, valued in excess of five billion dollars. Ethylene oxide is ordinarily used in the production of ethylene glycol (antifreeze), as well as detergents, ethanolamines, lubricants and many other commodity products.

The prior art has sought to develop increasingly selective catalysts for epoxide formation by, for example, modifying traditional silver (Ag) catalysts with a variety of promoters. U.S. Pat. Nos. 6,750,173, 5,905,053, and 5,663,385 describe the use of promoters to improve the selectivity of ethylene epoxidation catalysts. These patents generally teach adding alkali metals, alkali earth metals, transition metals, main group elements, and compositions containing the same to silver to improve the selectivity of the ethylene-to-ethylene oxide reaction.

Other prior art demonstrates that the reactivity of silver epoxidation catalysts and promoted-silver epoxidation catalysts remains unchanged regardless of which of Ag(111) and Ag(110) crystallographic planes predominate on the catalyst. Cambell (1985) *J. Catal.* 94: 436-444. Furthermore, structural differences in the silver epoxidation catalyst have been found to produce little to no effect on the selectivity and reactivity of the catalyst. Sajkowski et al. (1987) *Catal. Rev. Sci. Eng.* 29: 325-360.

More recently, the prior art suggests that crystal step edges are preferential to surface planes as epoxidation reaction sites. Briefly, a crystal is built from layers of atoms in a given order, the exterior of these crystals can be a plane of well-ordered atoms or molecules or can be a plane that bisects the well-ordered planes within the crystal. If the exterior of the crystal bisects ordered planes within a crystal then the transition between one ordered plane and the next is referred to as a step edge, analogous to a step edge on a flight of stairs wherein each stair is a well ordered plane of atoms. For example, the prior art suggests that step edges are more reactive than the silver surface planes for silver Ag(100) crystals. Kokalj et al, *Adsorption of Ethylene on Stepped Ag(n10) Surfaces* (Sep. 8, 2003) (Conference presentation at the 22nd European Conference On Surface Science) available at http://www.fzu.cz/activities/conferences/ecoss22/abstracts/17005.pdf; see also Massa, *Crystal Structure Determination* $2^{nd}$ ed., Springer, (2004), 20-22 (defining Miller indices and the surface plane notation). Correspondingly, in light of the catalytic reaction's insensitivity to crystallographic planes and the higher reactivity of step edges, one skilled in the art would understand that higher indices, e.g., Ag(410), would provide a better epoxidation catalyst because of the increase number of step edges.

Generally, the prior art neither sufficiently teaches nor suggests to one of ordinary skill in the art the use of Ag(100) as an epoxidation catalyst nor alkene epoxidation over Ag(100).

SUMMARY OF THE INVENTION

Disclosed herein are highly selective methods for making alkene oxides from alkenes in the presence of silver catalyst. These methods generally include converting an alkene (e.g., ethylene) to an alkene oxide (ethylene oxide or epoxide). According to one embodiment, the method includes reacting the alkene with oxygen in the presence of a silver catalyst under conditions suitable to produce a yield of the alkene oxide. According to another embodiment, the method includes passing an alkene-containing-feed over a silver catalyst under conditions suitable to yield a product gas containing the alkene and an alkene oxide (epoxide). In these embodiments, the silver catalyst can have a plurality of surface planes that are substantially Ag(100). Alternatively, the silver catalyst can be one that includes a silver nanocrystal having Ag(100) planes.

The disclosed methods convert alkene to alkene oxide with unexpectedly high selectivity for the alkene oxide product. While the prior art suggested that the reactivity and selectivity of a silver catalyst is not dependent on the crystallographic planes that are exposed, through the current invention it was unexpectedly observed that a Ag(100) catalyst extraordinarily increases the selectivity of the epoxidation reaction.

Additional features of the invention may become apparent to those skilled in the art from a review of the following detailed description, taken in conjunction with the drawings, the examples, and the appended claims.

BRIEF DESCRIPTION OF THE DRAWING FIGURES

For a more complete understanding of the disclosure, reference should be made to the following detailed description and accompanying drawings briefly described below.

While the disclosed methods include embodiments in various forms, it is not intended to limit the invention to the specific embodiments described and illustrated herein.

DETAILED DESCRIPTION OF THE INVENTION

Disclosed herein is a catalytic method of converting alkenes to epoxides. This method generally includes reacting alkenes with oxygen in the presence of a specific silver catalyst under conditions suitable to produce a yield of the epoxides. The specific silver catalyst is (or is derived from a silver catalyst precursor that includes) a silver nanocrystal having a plurality of surface planes, a substantial portion of which is defined by Miller indices of (100). The reaction is performed by charging a suitable reactor with this silver catalyst and then feeding the reactants to the reactor under conditions (e.g., temperature, pressure, flow-rate, etc.) sufficient to carry out the reaction. The reaction may be performed in batch, or as a continuous process that employs a recycle of any unreacted alkenes. Various embodiments of this general method are described in more detail below. The inventors have discovered that this specific silver catalyst has unexpectedly high selectivity for epoxide products. Consequently, the inventors have discovered that this general method (and its various embodiments) will result in extraordinarily high epoxide yields, heretofore unattainable.

According to one embodiment, the method includes reacting the alkene with oxygen in the presence of a silver catalyst under conditions suitable to produce a yield of the epoxide, wherein the silver catalyst has a plurality of surface planes that are substantially Ag(100).

According to another embodiment, the method includes passing an alkene-containing feed over a silver catalyst under conditions suitable to yield a product gas that includes unreacted alkene and an epoxide. Wherein, the silver catalyst has a plurality of surface planes, a substantial portion of which are Ag(100).

The conditions suitable to produce the epoxide or the silver catalyst include certain temperatures, and pressures, and can also include certain flow-rates, ratios of reactants, and introduction of catalyst inhibitors, for example. These and other conditions are described in more detail below.

The silver catalyst preferably includes silver nanocrystals. Nanocrystals means crystals of a material where at least one dimension is less than 1 μm. Herein, silver nanocrystals are not limited by their shape. All types of polyhedra are applicable as long as the polyhedra are substantially Ag(100). For example, see US 2005/0056118 A1, the disclosure of which is incorporated herein by reference, which generally discloses methods for manufacturing silver polyhedra. The term "substantially" when referring to Ag(100) means the faces (crystallographic planes) on the surface of the silver are defined by at least 50% Ag(100). Preferably, the faces are at least 75% Ag(100). Even more preferably, the faces are at least 90% Ag(100).

Two preferred examples of substantially Ag(100) polyhedra are silver nanowires and silver nanocubes. One example of substantially Ag(100) silver nanowires are the five-fold, twinned nanowires synthesized by the reduction of silver nitrate in ethylene glycol in the presence of poly(vinylpyrrolidone). See, Sun et al. (2002) *Science*, 298:2176, the disclosure of which is incorporated herein for the method of manufacturing shape selective silver nanocrystals. Preferably, the silver nanowires have a width of about 10 nm to about 1 μm, more preferably the nanowires have a width of about 10 nm to about 500 nm, even more preferably the nanowires have a width of about 25 nm to about 250 nm, still more preferably the nanowires have a width of about 50 nm to about 150 nm.

One example of substantially Ag(100) nanocubes are the cubes synthesized by the reduction of silver nitrate in 1,5-pentanediol in the presence of poly(vinylpyrrolidone). Preferably, the silver nanocubes have a width of about 10 nm to about 1 μm, more preferably the nanocubes have a width of about 20 nm to about 800 nm, even more preferably the nanocubes have a width of about 40 nm to about 600 nm, still more preferably the nanocubes have a width of about 50 nm to about 400 nm.

Figure 3:
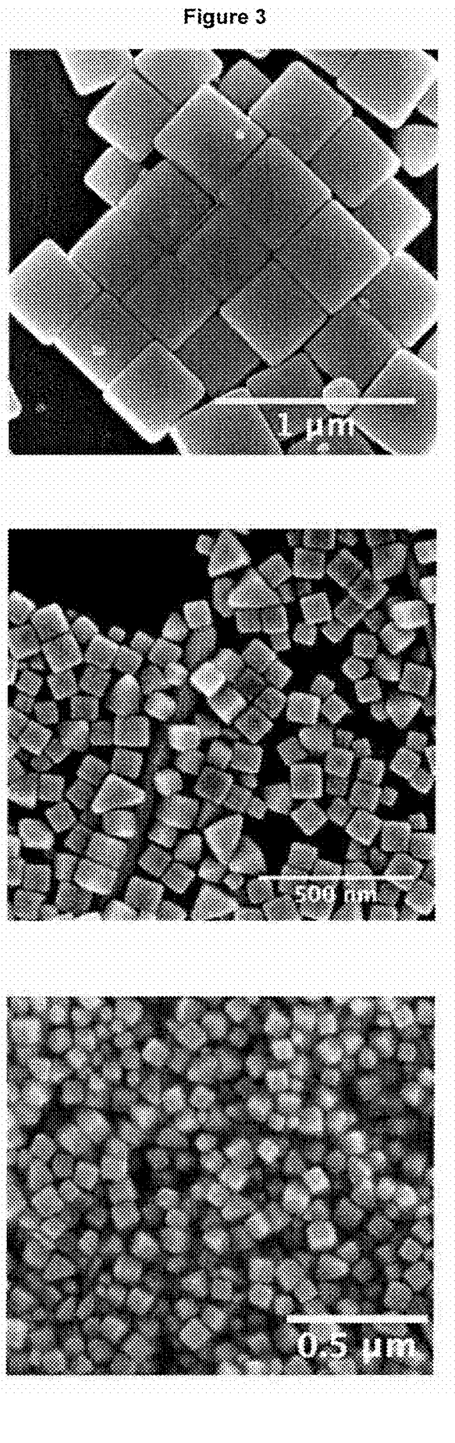
FIG. 3 is a series of representative SEM images of the 350 nm (top), 90 nm (middle), and 60 nm (bottom) silver nanocube catalysts used for the comparative study shown in FIG. 1.

Irrespective of the shape of the silver nanocrystal, the silver catalyst, preferably includes uniform silver nanocrystals. Herein, the silver catalysts includes silver nanocrystals that have substantially the same physical dimensions, e.g., uniform size distributions and uniform shape distributions. Substantially the same physical dimensions means that the physical size of the individual nanocrystals varies by less than about 50%. More preferably the size of the nanocrystals varies by less than 25%, still more preferably the size varies by less than 10%. FIG. 3 shows three samples of nanocrystals wherein the samples have different physical dimensions and wherein the nanocrystals of each individual sample have substantially the same physical dimensions, i.e., size and shape.

The silver catalysts applicable in the method disclosed herein can include a dopant. Herein, a dopant is any element or combination of elements added to the silver catalyst. Theoretically, the dopant does not interfere with the crystallographic planes of the silver catalyst. A non-exhaustive list of dopants includes alkaline earth metals, such as calcium or barium, alkali metals, such as cesium, rubidium, or potassium, transition metals, such as rhenium, and halides, such as fluorine or chlorine. These dopants can be added as elements, compounds, or compositions to the silver catalyst. Examples of dopants can be found in U.S. Pat. Nos. 5,905,053 and 5,663,385, and US 2004/0224841, the disclosures of which are incorporated herein by reference.

In the method disclosed herein, the silver catalyst is preferably supported on a catalyst support. Typically, but not exclusively, the silver catalyst is loaded onto a catalyst support. Catalyst supports can be any material that does not adversely affect the reaction of alkene with oxygen. Suitable catalyst supports include silica, silicates, alumina, aluminates, carbon, carbonates, carbides, diatomaceous earth, silicon carbide, zirconia, magnesia, silica-alumina, silica-magnesia, silica-titania, alumina-titania, alumina-magnesia, alumina-zirconia, thoria, silica-titania-zirconia, and various clays Additionally, the catalyst support can be glass wool, quartz, carborundum, or ion-exchange zeolites. The preferred support material comprises alumina preferably of a purity of at least 90 weight percent alumina and, more preferably, at least 98 weight percent alumina. Among the various available forms of alumina, α-alumina is the most preferred. The alumina catalyst support can be α-alumina, more specifically the alumina catalyst support can be an α-alumina foam (available from VESUVIUS HI TECH CERAMICS, Alfred Station N.Y.), even more specifically the alumina support can be an α-alumina foam monolith.

Often silver catalysts have non-catalytically active organic materials attached to the crystallographic planes due to the method of synthesis. These organic materials preferably are removed prior to the reaction of the alkene with oxygen. Alternatively, the reaction conditions can desirably affect the removal of these organic materials. One method for removing the organic materials is calcining the catalyst. Calcining refers to heating a material to bring about the thermal decomposition, or thermal desorption of the organic material from the surface of the catalyst. The calcination can include carrying out the thermal decomposition and/or thermal desorption in the presence of chemicals that facilitate the removal of the organic material. These chemicals can be for example oxygen, in a pure form or in a mixture, and/or hydrogen. The Ag(100) catalysts were preferentially calcined in the presence of oxygen. As noted previously, a dopant can be added to a catalyst but the dopant can additionally be added after the catalyst has been calcined. A second method for removing the organic materials is washing with a solvent, for example ethanol.

As noted above, one embodiment of the invention includes the catalytic conversion of an alkene to an epoxide in the presence of oxygen ($O_2$) and a silver catalyst ((Ag)). The catalytic conversion, or catalytic reaction, of ethylene can be expressed as the ideal chemical transformation in equation 1.

(1)

The equation is not intended to limit the applicable alkene. Alkenes can include ethylene, propylene, butene, butadiene and/or styrene. Preferably, the alkene is ethylene, butadiene, and/or styrene. The products from the epoxidation of ethylene, butadiene, and styrene are ethylene oxide, 3,4-epoxy-1-butene, and styrene oxide, respectfully.

The catalytic conversion of an alkene to an epoxide depends on the reaction conditions. Some of the reactions conditions include the composition of the feed, the reaction temperature, and the reaction pressure. The term "feed" generally refers to the reactive and inert chemicals and materials that are used to produce the epoxide. Feed specifically refers to the alkene and oxygen. Optionally, feed additionally refers to carrier gas(es) and/or excipients. The feed can be defined in part based on the ratio of the oxygen to alkene and optionally to the carrier gas. The oxygen:alkene ratio can be about 1:10 to about 10:1, preferably about 1:6 to about 8:1, more preferably about 1:2 to about 6:1, and even more preferably about 2:1 to about 4:1.

Suitable carrier gas(es) generally includes any gas that does not adversely affect the conversion of the alkene to the epoxide. Examples of suitable carrier gas include nitrogen, argon, helium, and mixtures thereof. Preferably, the carrier gas is nitrogen.

The feed can contain one or more excipients. Excipients are chosen to promote the conversion of the alkene to the epoxide and/or suppress unfavorable side reactions, e.g. ethylene to $CO_2$ and water and/or ethylene oxide to $CO_2$ and water. By way of example, excipients can be organic halides (e.g., ethylene dichloride, ethylene dibromide, ethylchloride, alkyl halides), or aryl halide, alkanes, aromatic hydrocarbons, amines, organometallic compounds or inorganic compounds. Examples of suitable excipients can be found in U.S. Pat. Nos. 2,279,469 and 2,279,470, the disclosures of which are incorporated herein by reference.

One reaction condition is the flow rate of the reactants, alkene and oxygen, through or over the catalyst. The flow rate of the reactants depends on a number of factors including the loading of the catalyst on the support, the volume of the catalyst and support, the size and shape of the catalyst, the type of support, the temperature of the reaction, the particular alkene, and the like. Herein, standardized cubic centimeters per minute (sccm) are used to describe the flow of the reactants over or through the catalyst. Alkene flow rates can be about 5 sccm to about 50 sccm. Oxygen flow rates can be about 5 sccm to about 100 sccm. In one embodiment, the alkene flow rate was 10 sccm, the oxygen flow rate was 60 sccm, and the nitrogen (carrier gas) flow rate was 30 sccm.

Another reaction condition is the reaction temperature. In all embodiments, the temperature can be about 100° C. to about 400° C., preferably about 175° C. to about 275° C., and more preferably about 230° C. to about 240° C. The temperature can be adjusted by heating the feed, the catalyst, the catalyst support, or any other material that can affect the temperature of the reaction. In one embodiment, the feed is heated and the temperature of the reaction is adjusted by adjusting the temperature of the feed. In another embodiment, the temperature of the catalyst and/or catalyst support is directly heated. In yet another embodiment both the feed and the catalyst and/or catalyst support are heated. Additionally, the flow rate, as discussed above, affects heat transfer and the temperature of the reaction.

Yet another reaction condition is the reaction pressure. The reaction pressure preferably is about 1 atmosphere (atm) to about 40 atm, more preferably about 1 atm to about 30 atm, and even more preferably about 1 atm to about 10 atm.

Figure 1:
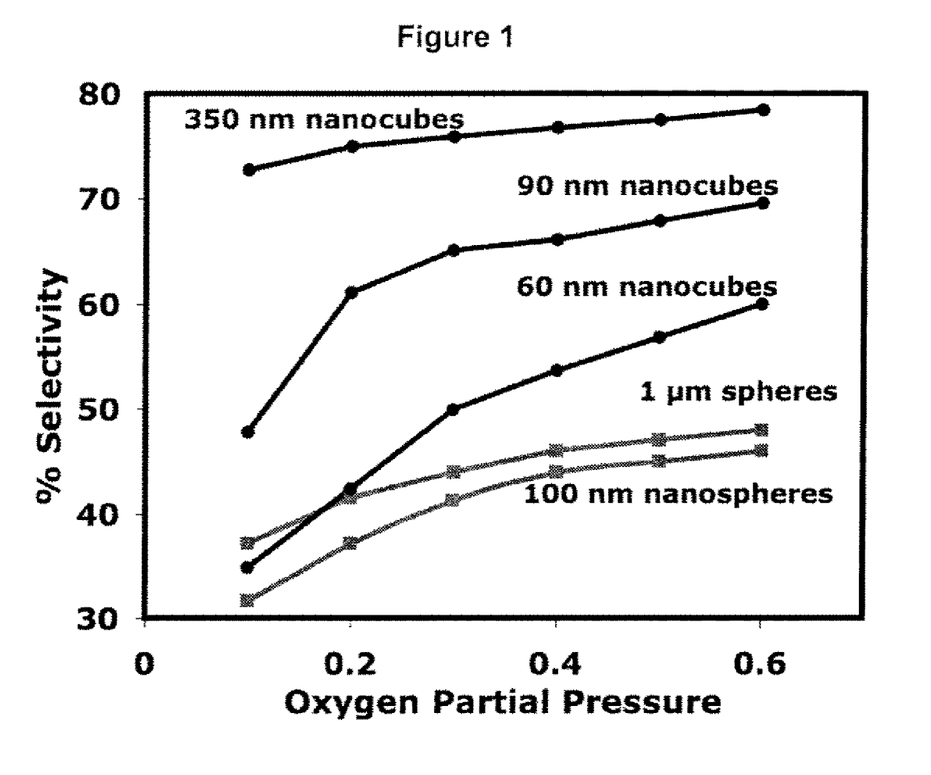
FIG. 1 is a comparison of the selectivity for ethylene epoxidation between silver nanocube catalysts having substantially Ag(100) crystallographic planes and comparative silver catalysts having substantially Ag(111) crystallographic planes. The selectivity for ethylene epoxidation is shown to vary based on the oxygen:ethylene ratio and the size of the nanocubes.

Extraordinarily, selectivities for ethylene oxide of at least 65% were observed when ethylene and $O_2$ were reacted in the presence of the herein described Ag(100) catalysts. Herein, "selectivity" is defined in terms of the potential epoxide from the reaction of an alkene with oxygen in the presence of a silver catalyst. In the case of ethylene, the selectivity (expressed as a percentage) is the moles of ethylene oxide produced per mole of ethylene consumed. Increasing the oxygen concentration, expressed as an increase in the oxygen:alkene ratio or an increase in the oxygen partial pressure, increases the selectivity for ethylene oxide, as shown in FIG. 1. The selectivity for epoxide can be greater than about 50%, 55%, 60%, 65%, 70%, 75%, 80%, 85%, 90%, 95%, and/or 99%.

The disclosed method can optionally include a recycling step. Specifically, after the feed passes through or over the catalyst it is described as the product or product gas. In a recycling step, unreacted alkene is separated from the epoxide product, carbon dioxide, and water, and then recycled to the feed. The reaction conditions can be adjusted to minimize the formation of carbon dioxide and water, which otherwise can result in unreacted alkene. The unreacted alkene is recycled to the feed, and can pass through or over the catalyst multiple times. The separation of the unreacted alkene from other materials in the product can be accomplished by conventional methods known by those having ordinary skill in the art. At steady state, with the recycle step, the disclosed method can be expected to achieve a conversion of about 10% to about 30%.

EXAMPLES

The following example is provided to illustrate the invention, but is not intended to limit the scope thereof. The catalytic conversion of ethylene to ethylene oxide was conducted the same way over five Ag(100) catalysts and one standard silver catalysts for comparative purposes. All studies were performed in a horizontally oriented tube reactor operated isothermally at 237° C. and atmospheric pressure. A 1.0 gram $\alpha$-$Al_2O_3$ foam monolith support (99.5%, Vesuvius Hi-Tech Ceramics) with surface area of 0.3 m$^2$/g was used in all experiments. The monolith was secured in a quartz reactor tube using quartz wool. Total inlet flow rate was kept constant at 100 sccm; gas flow rates were controlled using gas flow controllers and all gases used were the highest purity available. All catalysts were allowed to run at 10 sccm oxygen and ethylene and 80 sccm nitrogen until they reached steady state. The oxygen:ethylene ratio was then varied by increasing the oxygen flow rate, decreasing the nitrogen carrier gas flow rate while holding the ethylene flow rate constant. Product gases were analyzed in line with a Varian gas chromatograph (Varian CP 3800) equipped with a thermal conductivity detector and a flame ionization detector.

Comparative Catalyst: A comparative catalyst was a silver catalyst dominated by the Ag(111) surface made by standard impregnation methods. Generally, a pre-cleaned alumina ($Al_2O_3$) monolith was contacted with a silver nitrate ($AgNO_3$) solution with a small excess of silver compared to the desired loading. The monolith was then dried at 80° C. in air. The silver nitrate was then placed in a hydrogen atmosphere and heated to 300° C. for three hours. The final weight percent loading was verified by weighing the monolith before impregnation and after the silver nitrate was reduced to form silver particles. The final weight loading was 12.5%. The particles were spherical with sizes on the order about 1 μm as measured by SEM. A comparative catalyst with 100 nm nanospheres was produced by an analogous method.

Ag(100) Nanowires: Catalyst A included Ag(100) nanowires with a 75 nanometer (nm) width. Catalyst A was prepared by a seedless polyol process described by Sun et al. (2002) *Adv. Mater.* 14: 833-37, where silver nitrate ($AgNO_3$; 99.99%) is reduced in ethylene glycol (99.8% anhydrous) that was heated to 160° C. in the presence of poly(vinyl pyrrolidone) (PVP; average molecular weight=40,000). Silver nanowires 75 nm in diameter were made by heating five milliliters (mL) of ethylene glycol to 160° C. in a small flask. To the hot ethylene glycol was then added simultaneously, three mL of a $AgNO_3$ solution (made by dissolving 17 grams of $AgNO_3$ in one liter of ethylene glycol) and three mL of a PVP solution (made by dissolving 24 kilograms of PVP in one liter of ethylene glycol). The $AgNO_3$ and PVP solutions were added at a rate of 0.375 mL/min. During and after the addition, the solution was vigorously stirred for one hour while maintaining the temperature of the solution at 160° C. The solution was then cooled to room temperature and diluted 10-fold with acetone. Next, the solution was centrifuged at 2500 rotations per minute (rpm) for 20 minutes, to separate the reaction products from the ethylene glycol, and the supernatant was removed from or drained off of the reaction products. The silver nanowire product was then purified from the reaction products by dispersing the reaction products in deionized water and centrifuging at 2000 rpm for 20 minutes, the supernatant was removed and the procedure repeated until the supernatant was colorless.

Next, the supported nanowire catalyst was prepared using a concentrated solution of the silver nanowire catalyst in ethanol as an impregnation solution. The impregnation solution was then added to an $α-Al_2O_3$ foam monolith and the combination was dried at 70° C. to yield the supported catalyst Catalyst B included Ag(100) nanowires with a 175 nm width. The method that was used to produce catalyst 75 nanometers in diameter was used to produce catalyst 175 nanometers in diameter. Two differences were reducing the amount of PVP from 24 kilograms in one litter of ethylene glycol to six kilograms in one litter of ethylene glycol, and the addition rate was slowed to 0.2 mL/min. Otherwise the method of purifying the catalyst and preparing the supported catalyst were the same.

The results of catalytic conversions of ethylene to ethylene oxide in the presence of Catalysts A and B are compared with the conversion in the presence of the Ag(111) comparative catalyst and are shown in Table 1. For comparison purposes the reaction conditions were the same for all three catalysts and the oxygen:ethylene ratio was 6:1.

TABLE 1

| | NANOWIRES | | | |
|---|---|---|---|---|
| | Cat. A | Cat. B Width/Index | Comp. Cat. | |
| | 75 nm Ag(100) | 175 nm Ag(100) | 1 μm Ag(111) | |
| Selectivity | 53% | 63% | 46% | ethylene oxide produced per ethylene consumed |
| Conversion | $5.9 \times 10^{-2}$ | $3.0 \times 10^{-2}$ | $7.7 \times 10^{-3}$ | grams ethylene consumed per gram catalyst per minute |
| Yield | $4.9 \times 10^{-2}$ | $2.9 \times 10^{-2}$ | $5.7 \times 10^{-3}$ | grams ethylene oxide produced per gram of catalyst per minute |

Figure 2:
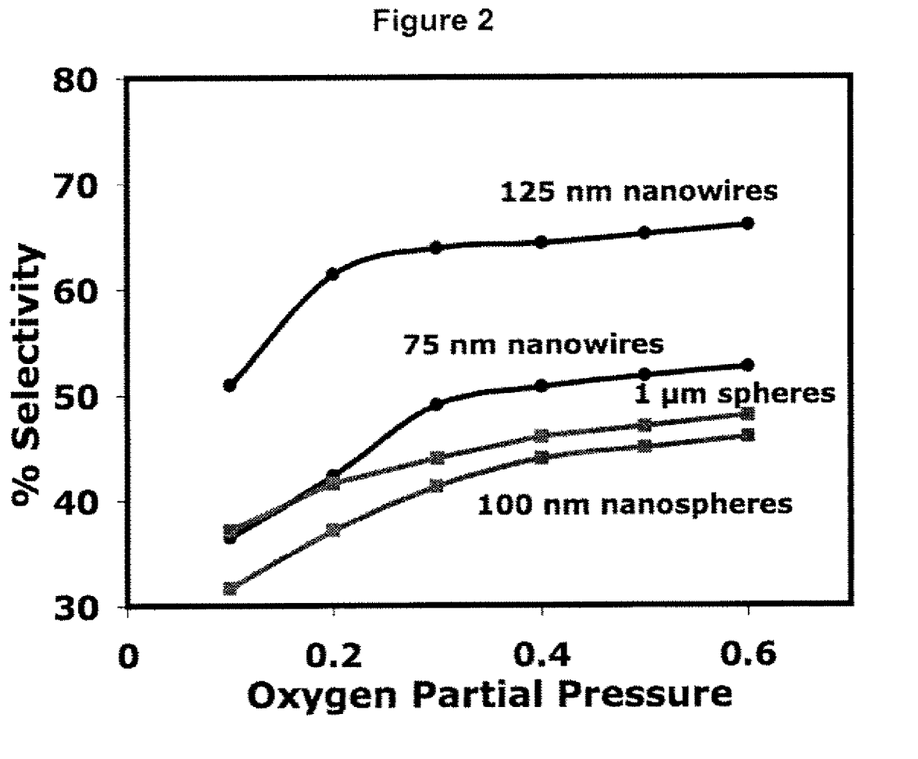
FIG. 2 is a comparison of the selectivity for ethylene epoxidation between silver nanowire catalysts having substantially Ag(100) crystallographic planes and comparative silver catalysts having substantially Ag(111) crystallographic planes. The selectivity for ethylene epoxidation is shown to vary based on the oxygen:ethylene ratio and the size of the nanowires.

The selectivity of catalytic conversion of ethylene to ethylene oxide for Ag(100) nanowire catalysts as a function of Oxygen partial pressure in the feed gas was measured and compared to the selectivity of comparative catalysts. FIG. 2 shows the results of selectivity studies for Ag(100) nanowire catalysts with widths of 75 nm and 175 nm and Ag(111) comparative catalysts with spherical diameters of 100 nm and 1 μm.

Ag(100) Nanocubes: Catalyst C included Ag(100) nanocubes with 60 nm edge lengths. Catalyst C was prepared by first heating 5 mL ethylene glycol and a magnetic stir bar in a 20 mL vial to 140-145° C. on a stirring hotplate. The vial was loosely capped and was maintained at the elevated temperature for one hour. Then 100 μL of a 30 mM HCl in ethylene glycol solution was added to the vial. This solution was mixed for 5-10 min. and then 3 mL of a 0.1M $AgNO_3$ (99% purity) in ethylene glycol solution and 3 mL of a 0.15M polyvinylpyrrolidone (55,000 M.W.) in ethylene glycol solution were added at a rate of 0.75 mL/min. Then the vial was loosely closed and the solution stirred for 24 hours and after 24 hours the vial was sealed and the solution turned tan/ocher over the course of 2-3 hours. The nanocubes were isolated as illustrated for the nanowires.

Catalyst D included Ag(100) nanocubes with 90 nm edge lengths. Catalyst D was prepared by the same method as Catalyst C but the aliquot of acid was reduced to 60 μL.

Catalyst E included Ag(100) nanocubes with 350 nm edge lengths. Catalyst E was synthesized by heating ethylene glycol (99.8% anhydrous) to 140-145° C. in a loosely capped vial for one hour and then adding 100 μL of a 30 mM HCl solution. Next, 3 mL of a 0.3M AgNO$_3$ solution and 3 mL of a 0.45M PVP solution were added at a rate of 0.75 mL/min. The nanocubes grew over the course of 2-3 hours resulting in a tan/ocher color. The nanocubes were isolated as illustrated for the nanowires.

The nanocubes were deposited on the alumina monoliths in the same manor as previously described.

The results of catalytic conversions of ethylene to ethylene oxide in the presence of Catalysts C, D, and E are compared with the conversion in the presence of the Ag(111) comparative catalyst and are shown in Table 1. For comparison purposes the reaction conditions were the same for all four catalysts and the oxygen:ethylene ratio was 6:1.

TABLE 2

| NANOCUBES | Cat. C | Cat. D | Cat. E | Comp. Cat. | |
| --- | --- | --- | --- | --- | --- |
| Size/Index | 60 nm Ag (100) | 90 nm Ag (100) | 350 nm Ag (100) | 1 μm Ag (111) | |
| Selectivity | 60% | 69.5% | 77.7% | 46% | ethylene oxide produced per ethylene consumed |
| Conversion | $1.2 \times 10^{-2}$ | $1.3 \times 10^{-2}$ | $2.4 \times 10^{-2}$ | $7.7 \times 10^{-3}$ | grams ethylene consumed per gram catalyst per minute |
| Yield | $1.1 \times 10^{-2}$ | $1.4 \times 10^{-2}$ | $2.9 \times 10^{-2}$ | $5.7 \times 10^{-3}$ | grams ethylene oxide produced per gram of catalyst per minute |

The selectivity of catalytic conversion of ethylene to ethylene oxide for Ag(100) nanocube catalysts as a function of Oxygen partial pressure in the feed gas was measured and compared to the selectivity of comparative catalysts. FIG. 1 shows the results of selectivity studies for Ag(100) nanocube catalysts with widths of 60 nm, 90 nm, and 350 nm and Ag(111) comparative catalysts with spherical diameters of 100 nm and 1 μm.

Figure 4:
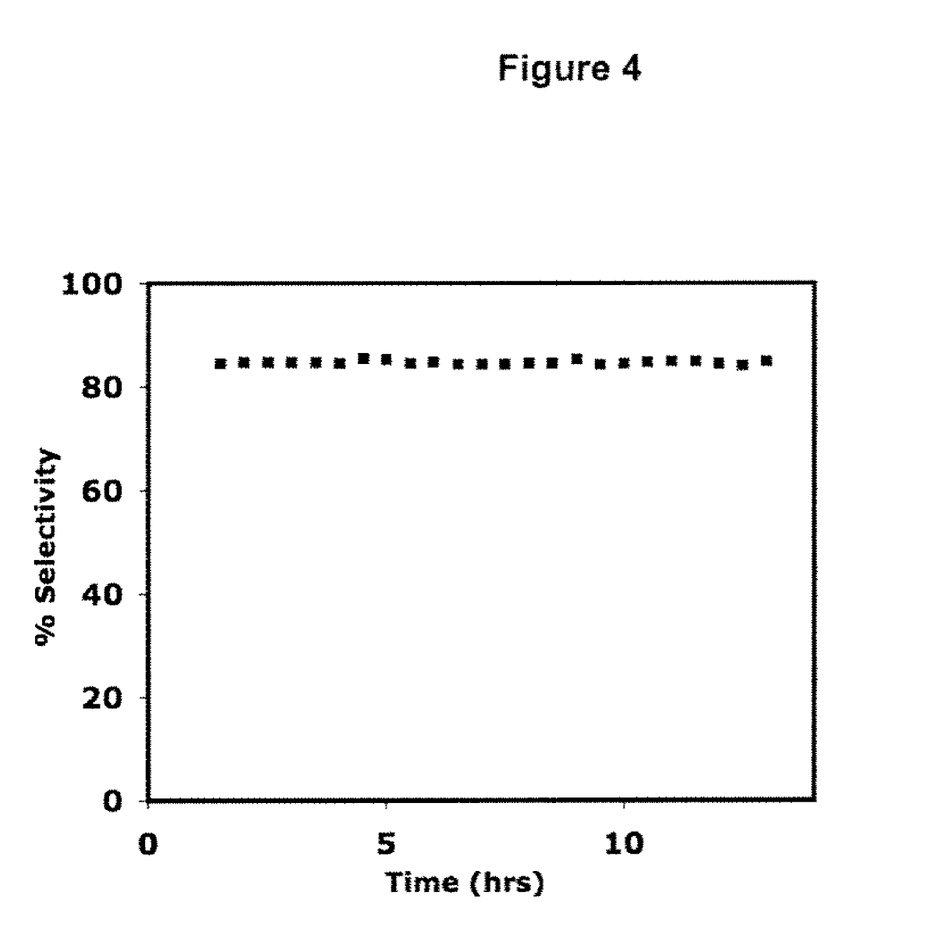
FIG. 4 is a plot of product selectivity for ethylene epoxidation as a function of time for a 350 nm nanocube catalyst at approximately 240° C. with 2 ppm vinyl chloride when the ratio of partial pressure of oxygen to partial pressure of ethylene was approximately 3:1.

The selectivity of catalytic conversion of ethylene to ethylene oxide as function of time was measured for a Ag(100) nanocube catalyst with a 350 nm nanocube width. The conditions for the catalytic conversion were 10 sccm ethylene, 30 sccm O$_2$, 60 sccm N$_2$ and 2 ppm vinyl chloride. FIG. 4 shows the results of the selectivity study and that here the selectivity of the catalytic conversion of ethylene was consistently greater than 80% for more than 10 hours.

These catalytic reactions clearly show the unexpected superiority of the silver epoxidation catalysts that are substantially Ag(100). The extraordinary selectivity of the epoxidation reactions using the Ag(100) catalysts was observed to be an unprecedented 20 to 50% increase over the prior art, culminating at an observed selectivity of about 78% for a pure silver catalyst.

The foregoing description is given for clearness of understanding only, and no unnecessary limitations should be understood therefrom, as modifications within the scope of the invention may be apparent to those having ordinary skill in the art.

What is claimed is:

1. A method of converting an alkene to an epoxide, the method comprising reacting the alkene with oxygen in the presence of a silver catalyst under conditions suitable to produce a yield of the epoxide, wherein the silver catalyst has a plurality of surface planes that are substantially Ag(100), and wherein the silver catalyst is selected from the group consistining of a silver nanowire, a silver nanocube, and a mixture thereof.

2. The method of claim 1 further comprising calcining the catalysts.

3. The method of claim 1 further comprising heating the silver catalyst to a temperature of about 100° C. to about 400° C.

4. The method of claim 1, wherein the conditions include an oxygen:alkene ratio of about 1:10 to about 10:1.

5. The method of claim 1, wherein the conditions include an oxygen flow rate of about 5 standard cubic centimeters per minute (cc/min) to about 75 cc/min and an alkene flow rate of about 5 cc/min to about 25 cc/min.

6. The method of claim 1, wherein the alkene comprises a primary alkene.

7. The method of claim 6, wherein the alkene is selected from the group consisting of ethylene, propylene, butene, butadiene, styrene, and mixtures thereof.

8. The method of claim 7, wherein the alkene is ethylene.

9. The method of claim 1, wherein the yield comprises a selectivity for the epoxide that is greater than about 50%.

10. The method of claim 1, wherein the silver catalyst comprises a silver nanowire.

11. The method of claim 10, wherein the silver nanowire has a width of about 25 nm to about 250 nm.

12. The method of claim 10, wherein the silver catalyst comprises a plurality of silver nanowires that have a uniform size distribution.

13. The method of claim 1, wherein the silver catalyst comprises a silver nanocube.

14. The method of claim 13, wherein the silver nanocube has a width of about 40 nm to about 600 nm.

15. The method of claim 13, wherein the silver catalysts comprises a plurality of silver nanocubes that have a uniform size distribution.

16. A method of converting an alkene to an epoxide, the method comprising passing an alkene-containing feed over a silver catalyst under conditions suitable to yield a product gas comprising the alkene and an epoxide, wherein the silver catalyst comprises a silver nanocrystal having a plurality of surface planes that are substantially Ag(100), wherein the feed comprises an alkene and O$_2$, and wherein the silver catalyst is selected from the group consisting of a silver nanowire, a silver nanocube, and a mixture thereof.

17. The method of claim 16 further comprising separating the alkene from the product gas, and combining the separated alkene with the feed.

18. The method of claim 16, wherein the feed further comprises a carrier gas selected from the group consisting of nitrogen, helium, argon, and mixtures thereof.

19. The method of claim 1, wherein at least 50% of the plurality of surface planes are Ag(100).

20. The method of claim 19, wherein at least 75% of the plurality of surface planes are Ag(100).

21. The method of claim 20, wherein at least 90% of the plurality of surface planes are Ag(100).

22. The method of claim 7, wherein the alkene is ethylene.

23. The method of claim 10, wherein the silver nanowire has a width of about 10 nm to about 500 nm.

24. The method of claim 10, wherein the silver nanowire has a width of about 50 nm to about 150 nm.

25. The method of claim 13, wherein the silver nanocube has a width of about 20 nm to about 800 nm.

26. The method of claim 13, wherein the silver nanocube has a width of about 50 nm to about 400 nm.

27. The method of claim 1, wherein the conditions include an oxygen:alkene ratio of about 1:6 to about 6:1.

28. The method of claim 1, wherein the conditions include an oxygen:alkene ratio of about 1:2 to about 6:1.

29. The method of claim 1, wherein the conditions include an oxygen:alkene ratio of about 2:1 to about 4:1.

30. The method of claim 16, wherein the silver catalyst further comprises a dopant.

31. The method of claim 30, wherein the dopant is selected from the group consisting of alkaline earth metals, alkali metals, transition metals, and halides.

32. The method of claim 16, wherein the feed further comprises one or more excipients capable of promoting conversion of alkene to epoxide.

33. The method of claim 32, wherein the excipient is selected from the group consisting of organic halides, aryl halides, alkanes, aromatic hydrocarbons, amines, organometallic compounds, and inorganic compounds.

34. The method of claim 3, comprising heating the silver catalyst to a temperature of about 175° C. to about 275°C.

35. The method of claim 3, comprising heating the silver catalyst to a temperature of about 230° C. to about 240° C.

36. The method of claim 1, wherein the conditions include a reaction pressure of about 1 atm to about 40 atm.

37. The method of claim 36, wherein the reaction pressure is about 1 atm to about 30 atm.

38. The method of claim 37, wherein the reaction pressure is about 1 atm to about 10 atm.

39. The method of claim 9, wherein the selectivity for the epoxide is greater than about 75%.

40. The method of claim 39, wherein the selectivity for the epoxide is greater than about 90%.

* * * * *